«12» United States Patent
Liu et al.

(10) Patent No.: US 9,809,843 B1
(45) Date of Patent: Nov. 7, 2017

(54) HIGH THROUGHPUT MEASUREMENT OF DNA BASE LESION REPAIR CAPACITY

(71) Applicants: Yuan Liu, Miami, FL (US); Yanhao Lai, Miami, FL (US); Ruipeng Lei, Miami, FL (US)

(72) Inventors: Yuan Liu, Miami, FL (US); Yanhao Lai, Miami, FL (US); Ruipeng Lei, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/253,412

(22) Filed: Aug. 31, 2016

(51) Int. Cl.
  *C12Q 1/68* (2006.01)
  *G01N 21/64* (2006.01)
  *G01N 21/29* (2006.01)
  *G01N 33/68* (2006.01)

(52) U.S. Cl.
  CPC ....... *C12Q 1/6827* (2013.01); *G01N 21/6428* (2013.01); *G01N 2021/6432* (2013.01); *G01N 2021/6439* (2013.01); *G01N 2201/062* (2013.01)

(58) Field of Classification Search
  None
  See application file for complete search history.

(56) References Cited

PUBLICATIONS

Maksimenko et al., "A molecular beacon assay for measuring base excision repair activities" 319 Biochemical and Biophysical Research Commuications 240-246 (2004).*
Edwards et al., "In Vitro Fluoreogenic Real-Time Assay of the Repari of Oxidative DNA Damage" 16 ChemBioChem 1637-1646 (Jun. 12, 2015)).*
Cafardi, Jennifer A, et al., "T4 endonuclease V: review and application to dermatology." Expert Opinion on Biological Therapy, 2008, 8(6): Abstract.
Nagel, Zachary D., et al., "Multiplexed repair assays for multiple lesions and multiple doses via transcription inhibition and transcriptional mutagenesis." PNAS, Apr. 22, 2014, E1823-E1832, www.pnas.org/cgi/doi/10.1073/pnas.1401182111.

\* cited by examiner

*Primary Examiner* — Nancy J Leith
(74) *Attorney, Agent, or Firm* — Saliwanchik, Lloyd & Eisenschenk (57) ABSTRACT

The invention pertains to methods for measuring DNA repair capacity of a test solution, for example, a cell lysate. The method can comprise incubating the test solution with a damaged DNA molecule and measuring the damaged DNA remaining at the end of the incubation. The damaged DNA used in the method comprises a marker attached to a first strand of the damaged DNA and a quencher attached to a second strand of the damaged DNA, characterized in that the quencher inhibits the release of a detectable signal from the marker when damaged DNA is in a double stranded form and the marker emits the detectable signal when at least a portion of the damaged DNA is in a single stranded form. The invention also provides screening assays for identifying one or more compounds from a plurality of compounds as an inhibitor of DNA repair mechanism.

19 Claims, 6 Drawing Sheets

HIGH THROUGHPUT MEASUREMENT OF DNA BASE LESION REPAIR CAPACITY

GOVERNMENT SUPPORT

This invention was made with government support under ES023569 awarded by the National Institutes of Health. The government has certain rights in the invention.

BACKGROUND OF INVENTION

Cells are continually exposed to factors, such as intracellular reactive species and environmental agents that are capable of causing DNA damage. Single bases in DNA can be chemically damaged by a variety of mechanisms, the most common ones being deamination, oxidation, and alkylation. These modifications can affect the ability of the base to hydrogen-bond, resulting in incorrect base-pairing, and, as a consequence, mutations in the DNA. For example, incorporation of adenine across from 8-oxoguanine (right) during DNA replication causes a G:C base pair to be mutated to T:A.

Agents that damage DNA include ionizing radiation such as gamma rays and X-rays, ultraviolet rays, especially the UV-C rays (~260 nm) that are absorbed strongly by DNA, but also the longer-wavelength UV-B that penetrates the ozone shield; high-reactive oxygen radicals produced during normal cellular respiration as well as by other biochemical pathways; chemicals in the environment, including some found in cigarette smoke; some plant and microbial products, e.g., the aflatoxins produced in moldy peanuts; and chemicals used in chemotherapy, especially chemotherapy of cancers.

The potentially mutagenic consequences of DNA damage are minimized by DNA repair pathways, which are broadly characterized into three forms: base excision repair (BER), mismatch repair (MMR), and nucleotide excision repair (NER). Deficiencies in DNA damage repair underlie the pathogenesis of cancer as well as many genetic disorders, such as Xeroderma pigmentosum, Cockayne syndrome, and Ataxia-telangiectasia.

BER is a cellular mechanism that repairs damaged DNA throughout the cell cycle. BER is important for removing damaged bases that could otherwise cause mutations by mispairing or lead to breaks in DNA during replication. BER is initiated by DNA glycosylases, which recognize and remove specific damaged or inappropriate bases. These are then cleaved by an endonuclease. The resulting single-strand break can then be processed by either short-patch (where a single nucleotide is replaced) or long-patch BER (where 2-10 new nucleotides are synthesized).

Steps and agents involved in BER include:
1. Removal of the damaged base (estimated to occur some 20,000 times a day in each cell) by a DNA glycosylase. There are at least 8 genes encoding different DNA glycosylases with each enzyme responsible for identifying and removing a specific kind of base damage.
2. Removal of its deoxyribose phosphate in the backbone, producing a gap. There are two genes encoding enzymes with this function.
3. Replacement with the correct nucleotide. This relies on DNA polymerase β.
4. Ligation of the break in the strand. Two enzymes are known that can do this; both require ATP to provide the needed energy.

Defects in a variety of DNA repair pathways lead to cancer predisposition. For example, deletion mutations in BER genes have been shown to result in a higher mutation rate in a variety of organisms, implying that loss of BER could contribute to the development of cancer. Indeed, somatic mutations in Pol β have been found in 30% of human cancers, and some of these mutations lead to transformation when expressed in mouse cells. Mutations in the DNA glycosylase MYH are also known to increase susceptibility to colon cancer.

To date, most of the cancer therapies that target DNA repair pathways are substances that inhibit DNA repair in cancer cells in order to enhance the effects of DNA-damaging chemotherapies and radiotherapies. Fewer attempts have been made to improve or accelerate DNA repair in order to reduce the consequences of DNA damage after it has occurred in order to prevent or treat disease, although compositions comprising T4 endonuclease V have been examined as a potential therapy for skin cancer (Cafardi and Elmets. Expert Opin. Biol. Ther., 8(6): 829-38 (2008)).

BER is an essential biological process for cells in combating a variety of DNA base lesions, which are the most common form of DNA damage in human cells. However, no simple, fast, and direct cellular-level high throughput measurement of BER capacity exists as of yet.

Current methods of BER measurement are either inaccurate (e.g. monitoring decreases in DNA damage) or too limited in their application (e.g. plasmid transfection-based measurement).

While plasmid transfection-based measurement of DNA repair in cells is a recent development, certain limitations prevent this method from being used at a high throughput scale. First, it involves the complex processes of tissue culture and plasmid transfection into single cultured mammalian cells. Furthermore, this technology is restricted by the limited availability of plasmids containing various types of DNA lesions and the inefficiency of introducing the plasmids into different types of mammalian cells. The cell transfection-based assay on DNA repair also prevents its application in measuring DNA repair capacity in human tissue.

Thus, there is a need for compositions and methods to measure DNA repair in cells and in animals, as well as for assays to quickly and accurately measure the capacity DNA base lesion repair in cells and animals.

BRIEF SUMMARY

The subject method provides simple, fast, and high throughput measurement of DNA base lesion repair capacity in whole cell lysates. In preferred embodiments, the subject invention provides a method to determine DNA repair capacity in a tissue sample. The tissue may be, for example, from a human. The human can be a healthy/control individual or an individual suffering from a disease, such as cancer.

The methods of the subject invention do not need complicated procedures involving cell culture and plasmid transfection. Instead, the methods can be performed easily using, for example, 96- or 384-well plates and a fluorescence plate reader with a temperature controller. Advantageously, the assay can be finished quickly, typically within one hour.

In certain embodiments, the methods described herein can be used as a high throughput screening platform for screening inhibitors of DNA repair, e.g., for development of anti-cancer drugs, or screening for environmental toxicants.

The subject invention further provides kits for human disease diagnosis, prognosis, prevention, and treatment. For example, kits for measuring DNA repair capacity as a biomarker for various purposes, such as prediction of cancer drug resistance and the development and progression of diseases, or for use in personal and precision medicine.

Accordingly, the subject invention provides methods for measuring DNA repair capacity of a test solution, for example, a cell lysate. In one embodiment, the method comprises incubating the test solution with a damaged DNA molecule and measuring the damaged DNA remaining at the end of the incubation. The damaged DNA used in the method comprises a marker attached to a first strand of the damaged DNA and a quencher attached to a second strand of the damaged DNA, wherein the quencher inhibits the release of a detectable signal from the marker when damaged DNA is in a double stranded form and the marker emits the detectable signal when at least a portion of the damaged DNA is in a single stranded form.

The invention also provides a screening assay for identifying one or more compounds from a plurality of compounds as an inhibitor of DNA repair mechanism.

DETAILED DESCRIPTION OF THE INVENTION

The subject invention provides materials and methods for a high throughput screening platform for screening inhibitors of DNA repair. One such embodiment can be used in anti-cancer drug development, while another can be used to screen for environmental toxicants.

The subject invention also provides materials and methods measuring DNA repair capacity. In one embodiment the subject invention provides methods for measuring DNA base excision repair (BER) capacity in a solution, for example, in a cell lysate. Cell lysates can be produced from cultured cells or cell/tissue samples from a subject.

Certain embodiments of the invention also provide a kit for performing the assays of the subject invention. The kit can comprise damaged DNA, as described herein, and reagents for carrying out the assays of the subject invention.

Accordingly, one embodiment of the invention provides a method for measuring DNA repair capacity of a test solution. The method comprises the steps of:
 a) incubating:
  i) a test reaction containing a damaged DNA and the test solution, and optionally,
  ii) a control reaction containing the damaged DNA and a control solution,
 characterized in that the control solution contains components that substantially repair the damaged DNA and the incubation is performed under conditions allowing the constituents of the test solution and the control solution to repair the damaged DNA;
 b) after the incubation of step a), measuring the amount of damaged DNA remaining in each of: i) the test reaction, and, if performed, ii) the control reaction; and
 c) determining the DNA repair capacity of the test solution based on:
  i) the amount of damaged DNA remaining in the test reaction after the incubation of step a) compared to the amount of damaged DNA added in the test reaction, and/or
  ii) the amount of damaged DNA remaining in the test reaction after the incubation of step a) compared to the amount of damaged DNA remaining in the control reaction after the incubation of step a);
 wherein the damaged DNA comprises a marker attached to a strand of the damaged DNA and a quencher attached to a second strand of the damaged DNA, such that the quencher inhibits the release of a detectable signal from the marker when damaged DNA is in a double stranded form and the marker emits the detectable signal when at least a portion of the damaged DNA is in a single stranded form.

In certain embodiments, the step of incubation of step a) is conducted at an appropriate temperature for an appropriate period of time. For example, the temperature can be 30° C. to 45° C., particularly, 35° C. to 40° C., and more particularly about 37° C. The incubation step can be performed for about 15 minutes to about two hours, particularly, about 20 minutes to about 1.5 hours, more particularly, about 25 minutes to about 1 hour, and even more particularly, about 30 minutes. The reaction mixture can comprise further reactants that facilitate the DNA repair reaction. Such reactants can be, for example, $Mg^{2+}$, dNTP, and ATP at appropriate concentrations.

The control solution can contain components that substantially repair the damaged DNA. For the purpose of this invention, the phrase "substantially repair the damaged DNA" means that the control solution contains a component that, during the incubation of step a), repairs at least about 80%, particularly, at least about 90%, more particularly, at least about 95%, and even more particularly, about 99% or more of the damaged DNA molecules added into the control reaction.

In certain embodiments, the damaged DNA comprises a marker attached to a first strand of the damaged DNA and a quencher attached to a second strand of the damaged DNA. The quencher inhibits the release of a detectable signal from the marker when damaged DNA is in a double stranded form; whereas, the marker emits a detectable signal when at least a portion of the damaged DNA is in a single stranded form. The presence of a portion of the damaged DNA in a single stranded faint indicates that the DNA is not repaired.

In one embodiment, the damaged DNA comprises a base lesion. "Base lesion" as used herein refers to DNA damage from, for example, oxidation, deamination, or alkylation of a nucleotide, wherein such modification causes distortion to the DNA helix structure.

In a preferred embodiment, the marker is a fluorescent dye and the quencher prevents fluorescence from the fluorescent dye. In certain embodiments, the marker and the quencher are each attached to opposite nucleotides of a nucleotide base pair (bp). In a further embodiment, the marker is attached to the nucleotide that is on the strand containing the base lesion in the damaged DNA and the quencher is attached to the nucleotide that is on the intact strand that is basepaired with damaged DNA strand.

Figure 1:
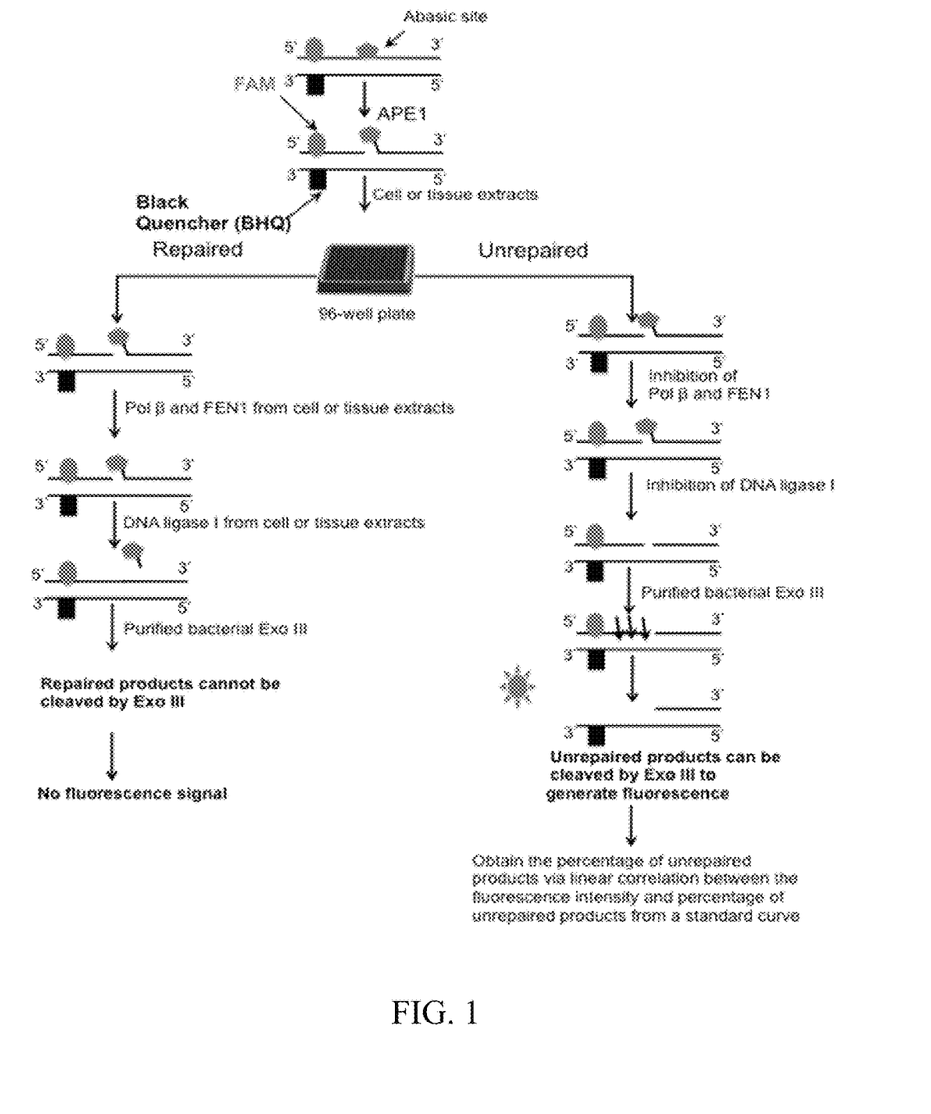
FIG. 1 shows a scheme of high throughput measurement of DNA repair capacity in cell and tissue extracts, as exemplified herein.

Accordingly, the step of measuring the amount of damaged DNA remaining in the test reaction and the control reaction is performed by measuring the signal emitted by the marker present on the damaged DNA (FIG. 1). In a typical embodiment, the signal is a fluorescent signal and the extent of the fluorescent signal in a reaction at the end of the incubation step a) and after the treatment with exonuclease corresponds to the extent of DNA repair. For example, higher fluorescent signal indicates lower DNA repair and vice versa.

The DNA repair capacity of a test solution can be measured in a variety of ways.

For example, the amount of damaged DNA remaining in the test reaction after the incubation of step a) can be compared to the amount of damaged DNA added in the test reaction before the incubation step a). The capacity of the test solution to repair damaged DNA can be expressed as a percentage of damaged DNA repaired during the incubation. For example, if 50% of damaged DNA remains in the test solution after the incubation step a), the capacity of the test solution to repair damaged DNA is 50%.

Also, the amount of damaged DNA remaining in the test reaction after the incubation of step a) can be compared to the amount of damaged DNA remaining in a control reaction after the incubation of step a). The capacity of the test solution to repair damaged DNA can be expressed as a ratio of damaged DNA repaired by the test solution to the damaged DNA repaired by the control solution. For example, if 50% of damaged DNA is repaired by the test solution after the incubation step a) and 90% damaged DNA is repaired by the control solution after the incubation step a), the capacity of the test solution to repair damaged DNA is 50 divided by 90, which is about 0.55 of the control solution.

Additional ways are known to a skilled artisan in which the capacity of a test solution to repair damaged DNA can be expressed, and such embodiments are within the purview of the invention.

In one embodiment, the test solution is a cell lysate. A cell lysate can be a lysate of a cultured cell or a lysate of a tissue obtained from an animal. In certain embodiments, the animal is a human. The tissue may be, for example, a diseased tissue. In one embodiment, the tissue is a cancerous tissue. As such, the methods of the invention can be utilized to determine the capacity of a cell, for example, a diseased cell, to repair damaged DNA, particularly, a damaged DNA containing base excision damage.

A further embodiment of the invention provides a screening assay to identify one or more compounds from a plurality of compounds as an inhibitor of DNA repair mechanism or not an inhibitor of DNA repair mechanism.

The screening assay of the invention comprises the steps of:
  a) incubating:
    i) a control reaction containing a damaged DNA and a test solution in the absence of any of the plurality of compounds, and
    ii) a plurality of test reactions, each test reaction containing the damaged DNA, the test solution, and at least one compound from the plurality of compounds;
  characterized in that the incubation is performed under conditions allowing the constituents of the test solution to repair the damaged DNA;
  b) after the incubation of step a), measuring the amount of damaged DNA remaining in the control reaction and each of the plurality of test reactions; and
  c) identifying each compound, or combination of compounds, in the plurality of compounds as:
    i) an inhibitor of DNA repair mechanism if the amount of damaged DNA remaining in the control reaction after the incubation of step a) is lower than the amount of damaged DNA remaining in the test reaction for the compound after the incubation of step a), or
    ii) not an inhibitor of DNA repair mechanism if the amount of damaged DNA remaining in the control reaction after the incubation of step a) is not lower than the amount of damaged DNA remaining in the test reaction for the compound after the incubation of step a);
  wherein the damaged DNA comprises a marker attached to a first strand of the damaged DNA and a quencher attached to a second strand of the damaged DNA,
  such that the quencher inhibits the release of a detectable signal from the marker when damaged DNA is in a double stranded form and the marker emits the detectable signal when at least a portion of the damaged DNA is in a single stranded form.

The aspects of the incubation of step a) discussed above in the context of the method to determine the capacity of a test solution to repair damaged DNA are also applicable to the screening assay of the invention. Similarly, the aspects of the damaged DNA and the techniques of measuring the damaged DNA left at the end of the incubation step a) discussed above in the context of the method to determine the capacity of a test solution to repair damaged DNA are also applicable to the screening assay of the invention.

In one embodiment of the screening assay, the test solution contains components repair at least about 80%, particularly, at least about 90%, more particularly, at least about 95%, and even more particularly, about 99% or more of the damaged DNA molecules added into the control reaction. Accordingly, the step of determining whether a compound from the plurality compounds is an inhibitor or not an inhibitor of DNA repair mechanism depends on the amount of damaged DNA remaining in the control reaction and the test reaction corresponding to the compound.

For example, the amount of damaged DNA remaining in the test reaction after the incubation of step a) can be compared to the amount of damaged DNA remaining in the control reaction after the incubation step a). If the amount of damaged DNA remaining in the test reaction after the incubation of step a) is higher than the amount of damaged DNA remaining in the control reaction after the incubation step a), the corresponding compound is an inhibitor of DNA repair mechanism in the test solution. On the other hand, if the amount of damaged DNA remaining in the test reaction after the incubation of step a) is not higher than the amount of damaged DNA remaining in the control reaction after the incubation step a), the corresponding compound is not an inhibitor of DNA repair mechanism in the test solution.

Further, efficiency of an inhibitor to inhibit damaged DNA repair mechanism can be expressed as the percentage reduction in damaged DNA repair in the test reaction compared to the control reaction in the screening assay of the invention.

In one embodiment of the screening assay of the invention, the test solution is a cell lysate. A cell lysate can be a lysate of a cultured cell or a lysate of a tissue obtained from an animal. In certain embodiments, the animal is a human and the tissue is a diseased tissue, for example, a cancerous tissue. As such, the methods of the invention can be utilized to determine the capacity of a cell, for example, a diseased cell, to repair damaged DNA, particularly, a damaged DNA containing base excision damage.

In one embodiment, the fluorescent marker is 6-carboxy-fluorscein (6-FAM) and the quencher is Black Hole Quencher-1 (BHQ-1). Dabcyl can also be used as a quencher.

Other combinations of quencher and fluorophore can be used. One embodiment uses a dual fluorescein pair (both fluorophore and quencher). Another specific option is to utilize a fluorescein/rhodamine pair. This results in a change in fluorescence color.

Other embodiments include the use of variants of fluorescein (e.g. 5 FAM, 6 FAM, and regular fluorescein) or other xanthene fluorophores (rhodamines, etc).

The following fluorescein-based molecules can be used: 5-fluorescein isothiocyanate (5-FITC), 6-fluorescein isothiocyanate (6-FITC), or 5/6-FITC mixed isomers, 5-carboxyfluoroscein (5-FAM), 6-carboxyfluorescein (6-FAM), 5/6-FAM mixed isomers, 5-carboxyfluorescein N-hydroxysuccinimidyl ester (5-fluorescein-SE), 6-carboxyfluorescein N-hydroxysuccinimidyl ester (6-fluorescein-SE), or 5/6-fluorescein-SE mixed isomers.

5-maleimide fluorescein (5-MF), 6-maleimide fluorescein (6-MF), or 5/6-MF mixed isomers, 5-iodoacetamidofluorescein (5-IAF), 6-iodoacetamidofluorescein (6-IAF), or 5/6-IAF mixed isomers can be used.

Finally, rhodamine 110 can be used because it is 1) green fluorescent (i.e. similar spectral characteristics) and 2) a xanthene dye (i.e. similar shape).

Thus, in addition to quenching, the assay can involve a change in fluorescent color. An example is when a green fluorescing molecule is close to a red fluorescing molecule. If a green-exciting light (i.e. blue) is introduced, the green fluorescence is the source of green light to excite the red fluorophore. When they drift, the green light can escape and not be a source of excitation for the red fluorophore. This is an example of a visually interpretable assay (i.e. red to green shift). In a related embodiment, red-fluorescing molecules to be used in accordance with the subject invention include, but are not limited to, Texas-Red, tetramethyl rhodamine, and xanthine-based dyes with red fluorescent emission spectrum.

The assay can involve one or more of the following:
a. LED or filtered white light excitation
    i. UV LED (≤380 nm) for blue-fluorescing fluorophores, and for most fluorophores in general (Blue, most others)
    ii. Blue/Cyan LED (450-495 nm) for green-fluorescing based fluorophores (Green/yellow)
    iii. Green LED (540-560 nm) for red-fluorescing fluorophores (Red)
    iv. Red LED (582 nm) for infrared read out
b. Read either by eye or with fluorimeter
    i. Eye
        1. Yes/No
        2. Semiquantitative scale
            a. Similar to pool chemistry where color/opacity scale is provided for comparison
    ii. Fluorimeter
        1. Quantitative via any available photon counting elements
            a. CMOS-based
            b. CCD-based
            c. Photodiode-based
            d. Photoresistor-based Advantageously, due to the narrow spectrum used to excite the dyes, interference due to visibly colored agents is effectively circumvented. For instance, with fluorescein excitation via blue light, hemoglobin cannot be seen because it does not scatter/reflect blue light.

Another embodiment utilizes chemilumenescent excitation (2,4-Dinitrophenyl oxalate via $H_2O_2$, for example) of the fluorophore. Advantageously, this makes the assay an instrument free assay.

A further embodiment of the invention provides a damaged DNA molecule (also referred to herein as "damaged DNA") useful for carrying out one or more assays of the subject invention. In one embodiment, the damaged DNA molecule described herein is a double stranded DNA molecule and comprises a marker attached to a first strand of the damaged DNA and a quencher attached to a second strand of the damaged DNA, characterized in that the quencher inhibits the release of a detectable signal from the marker when damaged DNA is in a double stranded form and the marker emits the detectable signal when at least a portion of the damaged DNA is in a single stranded form. In certain embodiments, the marker emits a fluorescent signal.

In further embodiments, the damaged DNA consists of 20 to 100 bp, particularly, 30 to 90 bp, more particularly, 40 to 80 bp, and even more particularly, 50 to 70 bp, and preferably about 60 bp.

In one embodiment, the damaged DNA comprises a base lesion. In a particular embodiment, the marker is a fluorescent dye and the quencher prevents fluorescence from the fluorescent dye. In a further embodiment, the marker is a fluorescent dye and the quencher prevents fluorescence from the fluorescent dye wherein the marker and the quencher are each attached to a nucleotide of a base paired nucleotides. In an even further embodiment, in the damaged DNA molecule the marker is attached to a nucleotide that is on the strand containing the base excision and the quencher is attached to a nucleotide that is on the intact strand of the damaged DNA.

Further embodiments of the invention provide kits useful for carrying out the methods and screening assay of the invention. The kits of the invention can comprise damaged DNA as described herein and, optionally, further comprise materials for carrying out the methods and screening assay of the invention.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The term "about" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

When ranges are used herein, such as for dose ranges, combinations and subcombinations of ranges (e.g., subranges within the disclosed range), specific embodiments therein are intended to be explicitly included.

All patents, patent applications, provisional applications, and publications referred to or cited herein are incorporated by reference in their entirety, including all figures and tables, to the extent they are not inconsistent with the explicit teachings of this specification.

Methods and Materials

Oligonucleotide Substrates

6-FAM (6-carboxyfluorescein)-conjugated DNA oligonucleotide substrates containing a tetrahydrofuran (THF), an abasic site analog, were designed and synthesized to mimic an abasic site i.e. abasic lesion that occurs in a random DNA sequence (Integrated DNA Technologies Inc., Coralville, Iowa). Template strands with Black Hole Quencher-1 (BHQ-1) was synthesized by Biosearch Technologies (Novato, Calif.). Substrates were constructed by annealing the oligonucleotide with a THF residue to its template strand at a molar ratio of 1:2, and the working concentration of substrate was prepared at 1 µM.

Cell Lysates Preparation

Cell pellets were re-suspended in lysis buffer that contained 10 mM Tris-HCl, pH 7.8, 200 mM KCl, 1 mM EDTA, 20% glycerol, 0.1% Nonidet P-40, 1 mM DTT with proteinase inhibitors (Roche Diagnostics Corporation, Indianapolis, Ind.). Cell suspension was subsequently subjected to rotation at 4° C. for 2 hours. After rotation, cell lysates were centrifuged at 14,000 rpm at 4° C. for 30 minutes to remove cell debris. The supernatant was recovered and further dialyzed into BER reaction buffer containing 50 mM Tris-HCl, pH 7.5, 50 mM KCl, 0.1 mM EDTA, 0.1 mg/ml bovine serum albumin, and 0.01% Nonidet P-40. Protein concentration of cell lysates was determined by Bradford assay. Cell lysates were aliquoted and stored at −80° C. for subsequent assay.

In Vitro Base Lesion Repair Capacity Assay

Substrates (25 nM) were pre-incubated with 25 nM purified APE1 at 37° C. for 15 minutes, and completely converted into ssDNA break intermediates for subsequent BER reactions. In vitro BER of a THF base lesion was performed by incubating APE1 precut substrate with 25 µg cell extracts in 10 µl-reaction mixtures that contained BER reaction buffer with 5 mM $Mg^{2+}$, 50 µM dNTP and 2 mM ATP in the absence or presence of inhibitors. Reaction mixtures were assembled on ice and incubated at 37° C. for 30 minutes.

Subsequently, 0.5 U EXO III (New England Biolabs, Ipswich, Mass.) was added into each reaction and incubated at 37° C. for 10 minutes to release fluorescence signal if the APE1 precut substrates were not fully repaired. Reaction mixtures were further incubated at 50° C. for another 30 minutes to ensure the complete release of 6-FAM conjugated unrepaired DNA fragments. EDTA was added into each reaction at a final concentration of 50 mM to terminate the reaction.

10 µl-reaction mixtures were then transferred to 386-well black plates (Thermo Fisher Scientific, Pittsburgh, Pa.) and subjected to fluorescence reading. Each substrates/lysate/inhibitor combination was run in triplicate.

Fluorescence Reading and Data Analysis 386-well plates were read at an excitation wavelength of 485±20 nm and an emission wavelength of 528±20 nm on a Synergy HTX Plate Reader (Bio-Tek, Winooski, Vt.). Data were exported to Excel for statistical analysis.

The fluorescence reading of each well needs to be abstracted by the reading from the well with 10 µl-BER reaction buffer alone before further data analysis. Normalized fluorescence data were averaged and plotted as "Average±Standard Deviation."

BER Capacity Assay

Measurement of BER capacity was performed by incubating APE1 precut substrate (25 nM) with 25 µg cell extracts in 10 µl-reaction mixtures that contained BER reaction buffer with 5 mM $Mg^{2+}$, 50 µM dNTP and 2 mM ATP in the absence or presence of inhibitors. Each reaction is set up in a 10 µl-reaction mixture that was composed by 5 µl of APE1 pre-cut substrates (25 nM) and 5 µl of a mixture of 25 µg cell extracts with individual inhibitors, such as pol β inhibitors NSC-666715 (200 µM), NSC-666719 (200 µM), NSC-124854 (200 µM).

The following examples illustrate procedures for practicing the invention. These examples should not be construed as limiting. It will be apparent to those skilled in the art that the examples involve use of materials and reagents that are commercially available from known sources, e.g., chemical supply houses, so no details respecting them are given.

Example 1—High Throughput Measurement of DNA Base Lesion Repair Capacity in Cell or Tissue Lysates FIG. 1 shows a scheme of high throughput measurement of DNA repair capacity in cell and tissue extracts, as exemplified herein.

In one embodiment, a method of high throughput measurement of DNA base lesion repair capacity in cell or tissue lysates comprises the following steps. A reaction is assembled in a microfuge tube on ice according to the parameters as set forth in Table 1. For multiple samples, a master mixture can be prepared.

TABLE 1

Exemplary reaction mixtures for high throughput measurement of DNA base lesion repair capacity in cell or tissue lysates

| Reaction Mixture | 1X Reaction Buffer | Substrate (Stock concentration: 1 µM) | $Mg^{2+}$ (Stock concentration: 1 mM) | dNTP (Stock concentration: 1 mM) | ATP (Stock concentration: 100 mM) | $ddH_2O$ | Total Vol. |
|---|---|---|---|---|---|---|---|
| 1X (one reaction) | 2.05 µl | 0.25 µl | 1 µl | 0.5 µl | 0.2 µl | 1 µl | 5 µl |
| 100X (ten reactions) | 205 µl | 25 µl | 100 µl | 50 µl | 20 µl | 10 µl | 500 µl |

5 µl of substrates were added into each well of a 96-well black plate for subsequent enzymatic reactions. 96-well black plates were kept at room temperature until its incubation at 37° C. 25 µg cell extracts (up to 4 µl) were added into each well of the 96-well plate and the plate was incubated at 37° C. for 30 minutes. Purified 1 µl of 50 nM APE1 (final concentration of 5 nM) was added into reaction mixtures in each well and reaction mixtures were incubated at 37° C. for 15 minutes to cleave unrepaired abasic sites in the substrates. 0.5 U EXO III was added into each reaction and incubated at 37° C. for 10 minutes to release fluorescence signal.

The reaction mixtures were incubated at 50° C. for an additional 30 minutes to ensure the complete release of 6-FAM labeled unrepaired DNA substrates. EDTA was added into each reaction at a final concentration of 50 mM to terminate the reactions and fluorescence readings were taken at an excitation wavelength of 485±20 nm and an emission wavelength of 528±20 nm on a Synergy HTX Plate Reader. The data was exported for statistical analysis. The fluorescence reading of each well was adjusted by subtracting background reading signals from a control containing substrate along with cell extract. Normalized fluorescence data were averaged and plotted with corresponding statistical errors.

Note that a standard curve of the capacity (measured by fluorescence) of BER reconstituted by purified APE1, pol β, FEN1 and LIG I (premixed with substrates) to the percent of repaired products, were made for calculating the capacity and scores of BER capacity in cell or tissue lysates.

Figure 2:
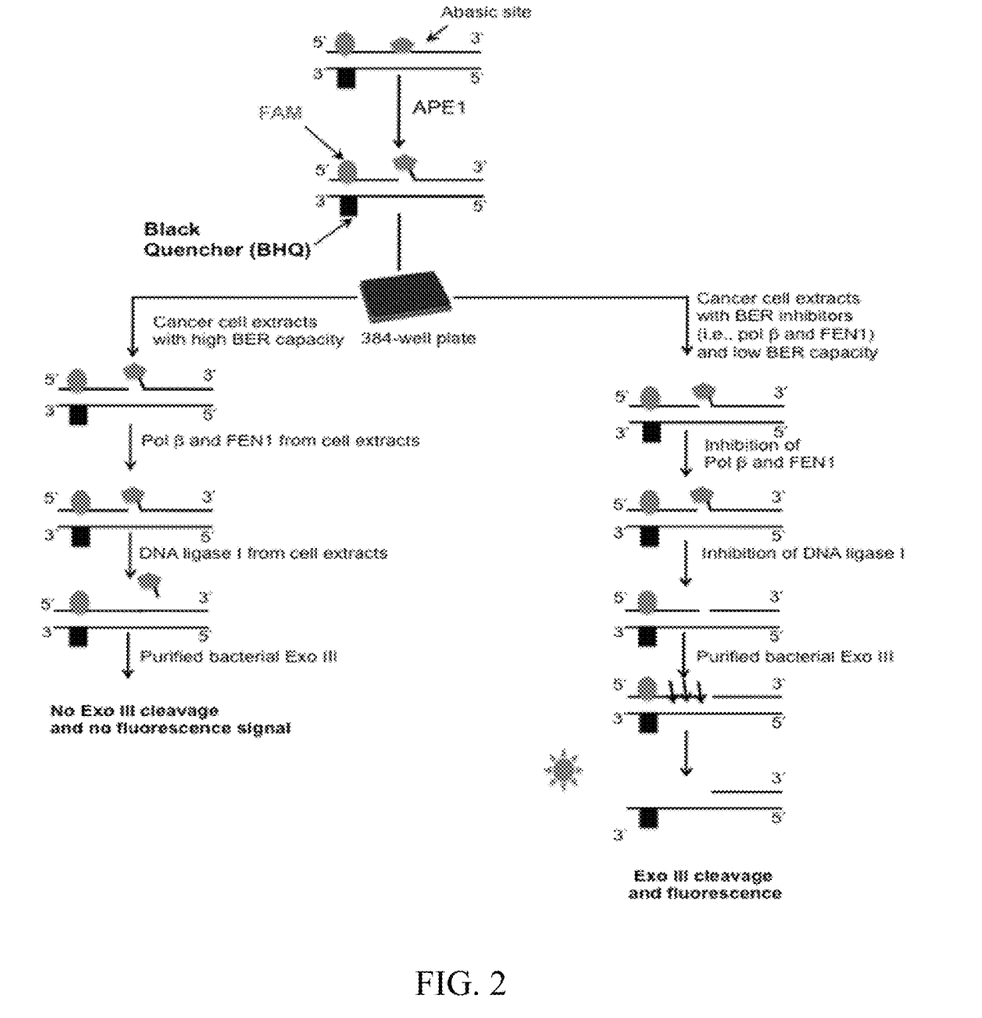
FIG. 2 shows a scheme of high throughput screening of inhibitors for DNA base lesion repair in cancer cell lysates, as exemplified herein.

Example 2—High Throughput Screening of Inhibitors for DNA Base Lesion Repair in Cancer Cells FIG. 2 shows a scheme of high throughput screening of inhibitors for DNA base lesion repair in cancer cell lysates, as exemplified herein.

In one embodiment, a method of high throughput screening of inhibitors for DNA base lesion repair capacity in cancer cells comprises the following steps. 25 nM substrate containing an abasic site was incubated with 5 nM purified APE1 at 37° C. for 15 minutes to generate single-strand DNA (ssDNA) break intermediates for subsequent BER reactions. Reactions were assembled in a microfuge tube on ice according to measurements in Table 2 and the following steps. For multiple samples, master mixture can be prepared.

TABLE 2

Exemplary reaction mixtures for high throughput measurement of DNA base lesion repair capacity in cancer cell extracts

| Reaction Mixture | 1X Reaction Buffer | Substrate (Stock concentration: 1 µM) | $Mg^{2+}$ (Stock concentration: 1 mM) | dNTP (Stock concentration: 1 mM) | ATP (Stock concentration: 100 mM) | APE1 (50 nM stock, freshly made) | Total Vol. |
|---|---|---|---|---|---|---|---|
| 1X (one reaction) | 2.05 µl | 0.25 µl | 1 µl | 0.5 µl | 0.2 µl | 1 µl | 5 µl |
| 100X (ten reactions) | 20.5 µl | 2.5 µl | 10 µl | 5 µl | 2 µl | 10 µl | 50 µl |

1X reaction buffer: 50 mM Tris-HCl (pH 7.5), 50 mM KCl, 0.1 mM RDTA, 0.1 mg/ml bovine serum albumin, and 0.01% Nonidet P-40.

5 µl of APE1 pre-cut substrates were added into 384-well black plates for subsequent enzymatic reactions and the plates were incubated at room temperature until its incubation at 37° C. 25 µg cell extracts (up to 4 µl) were added into each well of the plate. 1 µl of DMSO-dissolved inhibitors was added into each well with both APE1 pre-cut substrates and cell extracts. Reaction mixtures are assembled on ice and incubated at 37° C. for 30 minutes. 1 µl of DMSO alone was set up as "No inhibitor" control.

0.5 U EXO III was added into each reaction and incubated at 37° C. for 10 minutes to release fluorescence signal. Reaction mixtures were incubated at 50° C. for additional 30 min to ensure the complete release of 6-FAM conjugated unrepaired DNA substrates. EDTA was added into each reaction at a final concentration of 50 mM to terminate the reactions. Fluorescence readings were measured at excitation wavelength of 485±20 nm and emission wavelength of 528±20 nm on Synergy HTX Plate Reader. Data were exported for statistical analysis. The fluorescence reading of each well were adjusted by subtracting background reading signals from a control containing substrate along with cell extract. Normalized fluorescence data were averaged and plotted with corresponding statistical errors.

It is preferred to use several controls for each set of experiments, including buffer control that contained 10 µl-BER reaction buffer alone, substrate only control that contained 25 nM substrates in 10 µl-BER reaction buffer, APE1 pre-cut control with or without EXO III. Substrate along with cell extract without Exo III control is also needed.

Additionally, 50 µM-200 µM of compounds, NSC-666715, NSC-666719, NSC-124854 can inhibit DNA polymerase β is used for validating the inhibition of the method in VCap cell extracts. 1 µl DMSO does not affect Exo III activity and alter the intensity of fluorescence, while it was found that pol β inhibitors do not exhibit any inhibitory effects on Exo III activity.

Figure 3:
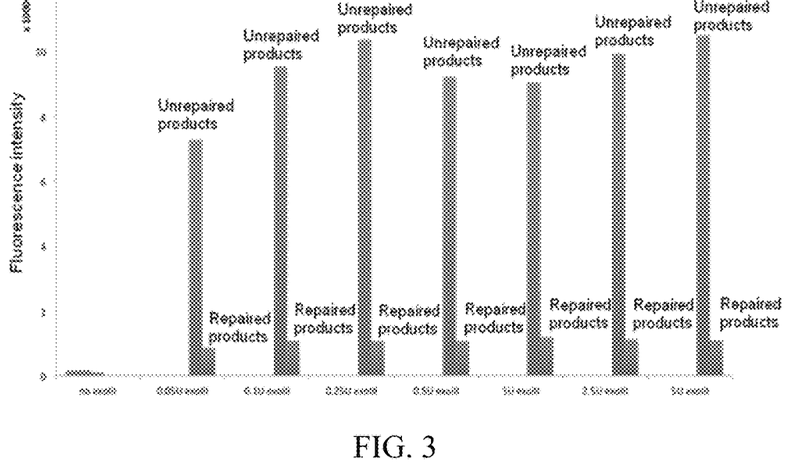
FIG. 3 shows measurement of the capacity of base excision repair reconstituted by purified repair enzymes.
Figure 4:
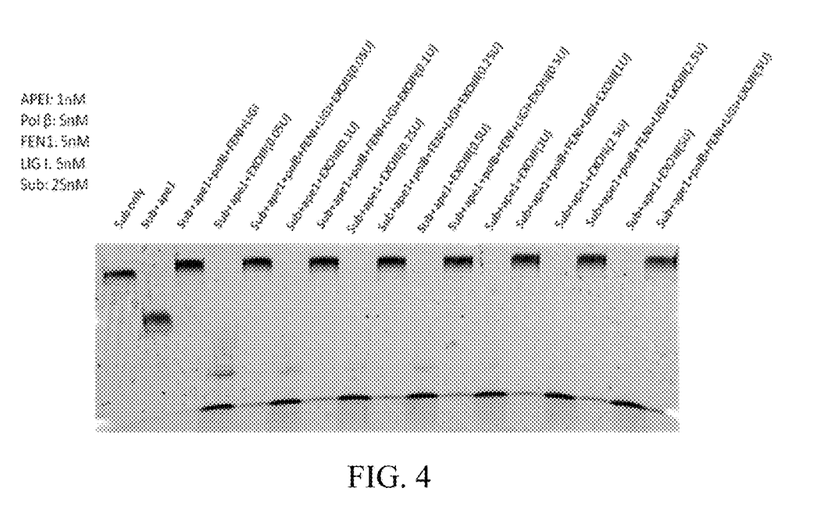
FIG. 4 shows measurement of capacity of BER reconstituted by purified repair enzymes.

Example 3—Measurement of the Capacity of Base Excision Repair Reconstituted by Purified Repair Enzymes Repaired products resulted in low fluorescence intensity at 1×10$^5$, whereas unrepaired products led to up to fluorescence at 9-10×10$^5$ (FIG. 3). The gel results showed that fluorescence intensity of 1×10$^5$ indicated 100% of abasic lesions were repaired, and the intensity of 9-10×10$^5$ indicated 0% of abasic lesions was repaired (FIG. 4).

Example 4—Measurement of BER Capacity in Prostate Cancer Cell Extracts (VCap Cells)

Figure 5:
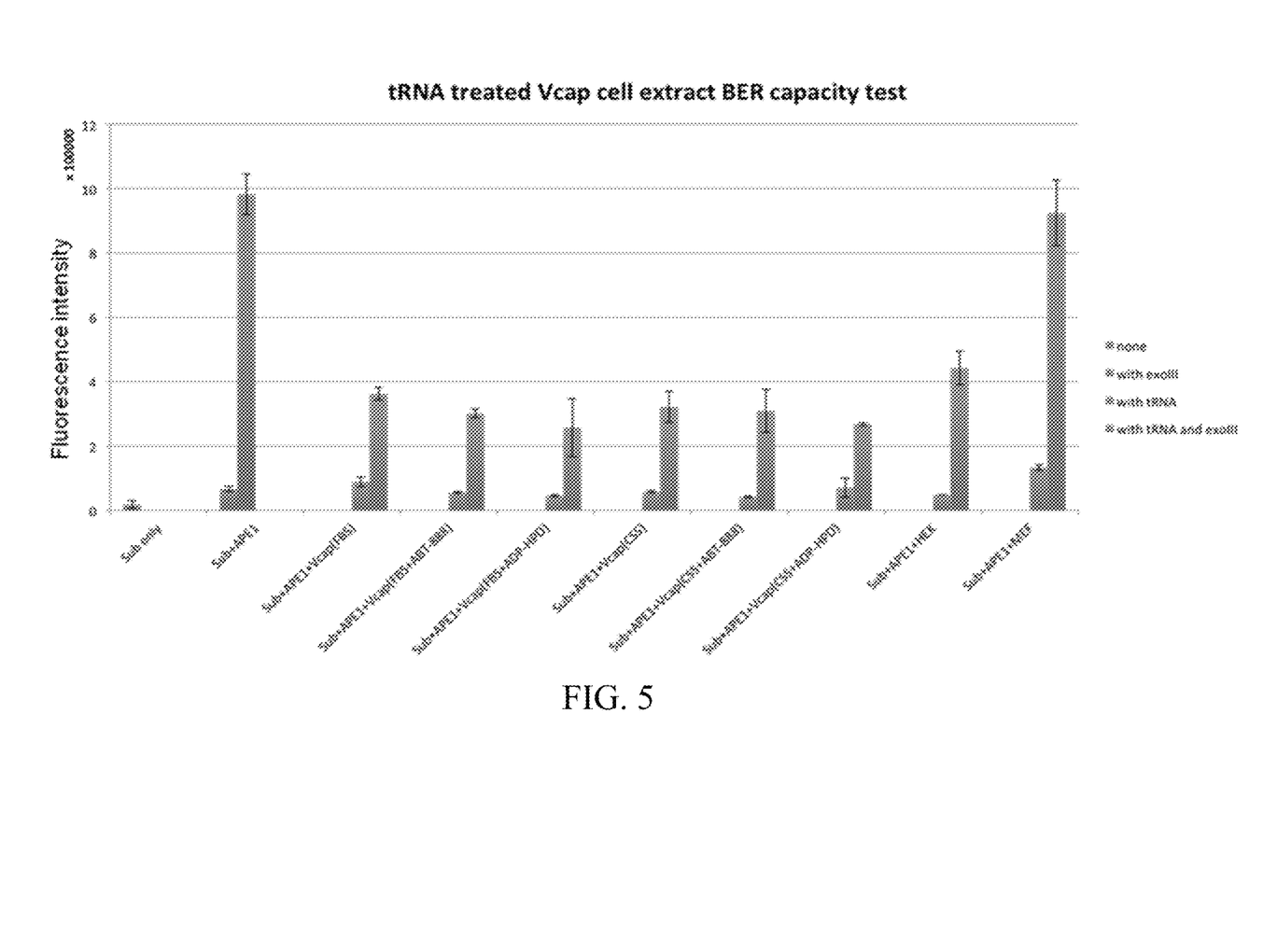
FIG. 5 shows BER capacity in VCaP, HEK293k and mouse embryonic fibroblast cell extracts.

Employing the assay described herein, the capacity of prostate cancer (VCaP) cell extracts treated under various experimental conditions was measured. The results showed BER capacity of VCaP cell extracts was higher than that of HEK293 and mouse embryonic fibroblast cell extracts (FIG. 5). However, no significant difference in BER capacity was detected among VCaP cell extracts under various treatments (FIG. 5).

Figure 6:
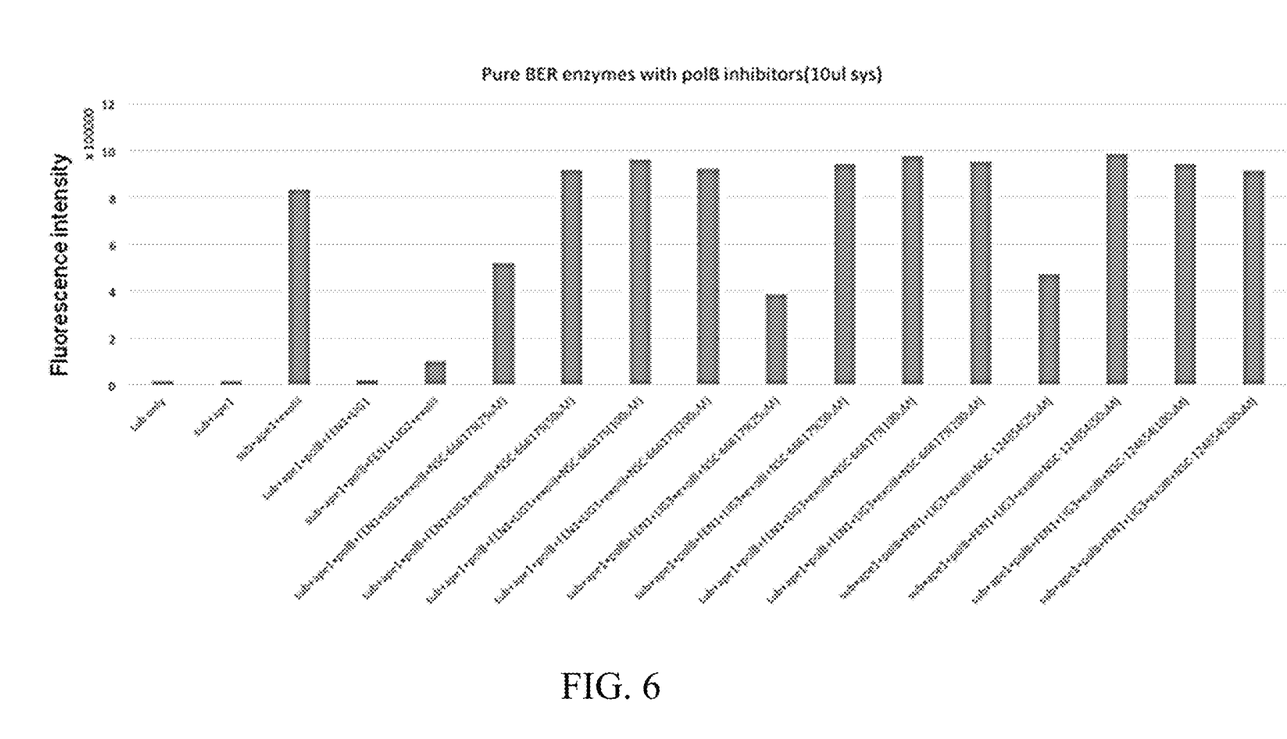
FIG. 6 shows the effects of pol β inhibitors on the capacity of BER reconstituted by purified BER enzymes.
Figure 7:
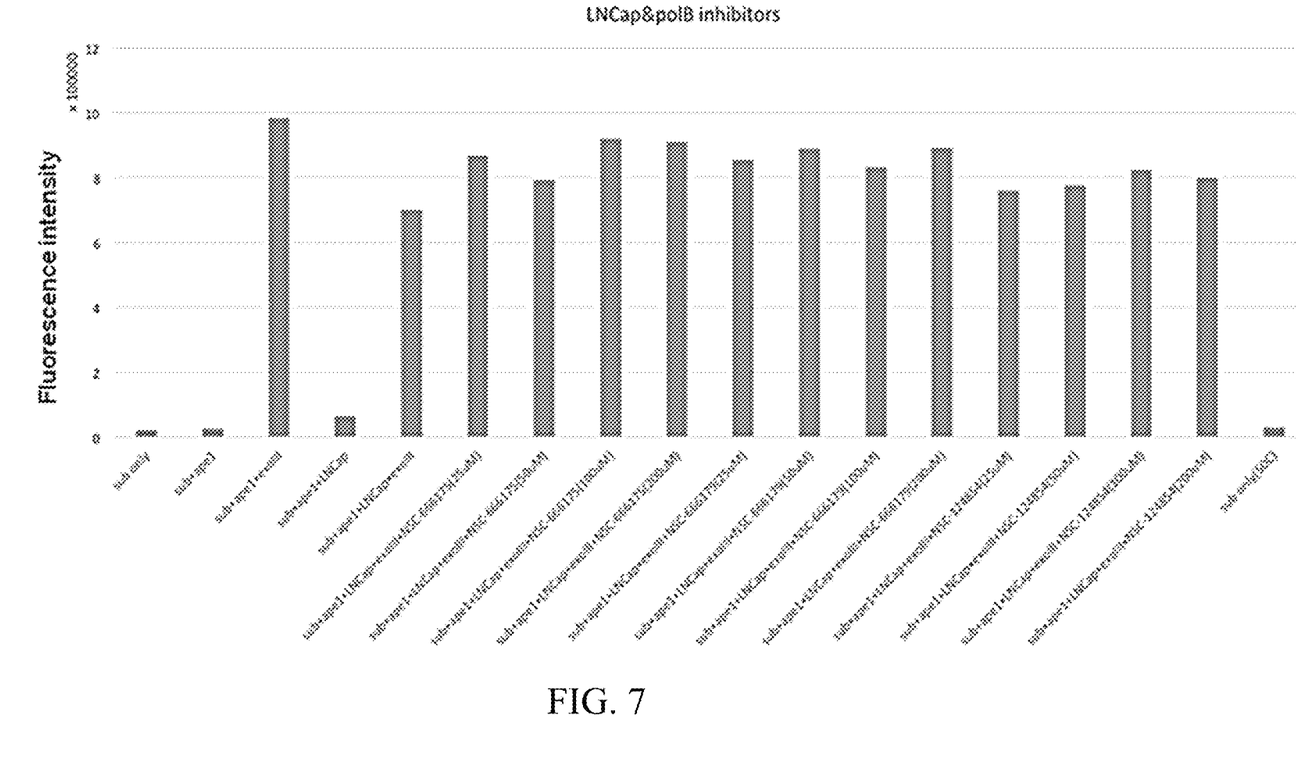
FIG. 7 shows the effects of pol β inhibitors on the capacity of BER of prostate cancer (LNCaP) cell extracts.

Measurement of the effects of the inhibitors of DNA polymerase β (pol β) on BER capacity. The effects of pol β inhibitors, NSC-666715, NSC-666719 and NSC-124854 on the capacity of BER reconstituted by purified repair enzymes and prostate cancer cell extracts were determined. The results showed that pol β inhibitors effectively reduced the capacity of BER reconstituted by APE1, pol β, FEN1 and LIG I by 4 to 10-fold (FIG. 6) indicating the high efficiency of inhibition of DNA repair by pol β inhibitors. However, their effects on reducing BER capacity of prostate cancer (LNCaP) were not significant (FIG. 7).

Example 5—Fast, High Throughput Assay for Measuring Total Capacity of DNA Base Lesion Repair Pathway A simple, fast, high throughput assay on measuring the total capacity of DNA base lesion repair pathway is provided. Good reproducibility and sensitivity in measuring capacity of BER reconstituted by purified enzymes as well as BER capacity in human cancer cell extracts is exhibited by the methods described herein. These methods can be used for determining total DNA repair capacity for screening DNA repair inhibitors for anti-cancer drug development, total DNA repair capacity in human population, human patient tissue, DNA repair capacity at specific genes and gene promoters as well as genomic regions as a biomarkers used for personalized medicine and precision medicine. The assay can be easily performed using 96- or 384-well plates with a fluorescence plate reader with a temperature controller. The assay for one 96-well or 384-well plates can be finished within 2 hours. In addition, the assays described herein do not need amplification of DNA by real-time PCR, which usually takes 3-5 hours. Moreover, the assays described herein measures total DNA repair capacity in lysed cell and tissue extracts without need of time consuming steps, such as culturing the cells and tissues and flow cytometry.

The methods described herein can be used in a high throughput screening platform for screening inhibitors of DNA repair in prostate cancer cell extracts as well as in methods for screening environmental toxicants that inhibit DNA repair for prevention environmentally-induced human diseases. The compounds identified as such can be used for cancer treatment.

The methodology can also be used to develop high throughput assays for other DNA repair pathways, for example, nucleotide excision repair and mismatch repair pathway. Further, the methods can be used in assays for the measurement of DNA repair capacity in human patient tissue as a biomarker for prediction cancer drug resistance and development and progression of diseases. Further, the methods can be used in assays for the measurement of DNA repair capacity in specific genome regions such as genes and promoter regions of an individual to show the polymorphic variations in DNA repair capacity of individuals in specific genes and sequences of human genome. As such, the methods described herein can be used in personalized medicine.

We claim:

1. A method for measuring DNA repair capacity of a test solution, the method comprising the steps of:
    a) incubating
        i) a test reaction containing a damaged DNA comprising:
            a marker attached to a first strand of the damaged DNA and
            a quencher attached to a second strand of the damaged DNA, wherein the quencher inhibits the release of a detectable signal from the marker when the damaged DNA is in a double-stranded form, and the test solution, and optionally,
        ii) a control reaction containing the damaged DNA and a control solution,
    under conditions allowing the constituents of the test solution and the control solution to repair the damaged DNA such that the repaired DNA is double-stranded and the quencher inhibits the release of a detectable signal from the marker in the repaired DNA;
b) detecting a signal emitted from the marker released from the damaged DNA if the damaged DNA is not repaired;
c) measuring the amount of damaged DNA remaining not repaired in each of: i) the test reaction, and, if performed ii) the control reaction; and
d) determining the DNA repair capacity of the test solution based on:
i) the amount of damaged DNA remaining not repaired in the test reaction after the incubation of step a) compared to the amount of damaged DNA added in the test reaction, and/or
ii) the amount of damaged DNA remaining not repaired in the test reaction after the incubation of step a) compared to the amount of damaged DNA remaining not repaired in the control reaction after the incubation of step a).

2. The method of claim 1, wherein the damaged DNA comprises a base lesion.

3. The method of claim 1, wherein the marker is a fluorescent dye and the quencher prevents fluorescence from the fluorescent dye.

4. The method of claim 1, wherein the marker and the quencher are each attached to opposite nucleotides of a base pair.

5. The method of claim 4, wherein the marker is attached to the nucleotide that is on the strand containing the base lesion in the damaged DNA and the quencher is attached to the nucleotide that is on the intact strand of the damaged DNA.

6. The method of claim 1, wherein the test solution is a cell lysate.

7. The method of claim 6, wherein the cell lysate is from a cancerous cell.

8. A screening assay to identify one or more compounds from a plurality of compounds as an inhibitor of DNA repair mechanism or not an inhibitor of DNA repair mechanism, the screening assay comprising the steps of:
a) incubating
i) a control reaction containing a damaged DNA comprising:
a marker attached to a first strand of the damaged DNA and
a quencher attached to a second strand of the damaged DNA, wherein the quencher inhibits the release of a detectable signal from the marker when the damaged DNA is in double-stranded form, and the test solution in the absence of any of the plurality of compounds, and
ii) a plurality of test reactions, each test reaction containing the damaged DNA, the test solution, and one of the plurality of compounds;
under conditions allowing the constituents of the test solution to repair the damaged DNA such that the repaired DNA is double-stranded and the quencher inhibits the release of a detectable signal from the marker on the repaired DNA;
b) detecting a signal emitted from the marker released from the damaged DNA if the damaged DNA is not repaired;
c) measuring the amount of damaged DNA remaining not repaired in the control reaction and each of the plurality of test reactions; and
d) identifying each compound in the plurality of compounds as:
i) the inhibitor of DNA repair mechanism if the amount of damaged DNA remaining not repaired in the control reaction after the incubation of step a) is lower than the amount of damaged DNA remaining not repaired in the test reaction for the compound after the incubation of step a), or
ii) not the inhibitor of DNA repair mechanism if the amount of damaged DNA remaining not repaired in the control reaction after the incubation of step a) is not lower than the amount of damaged DNA remaining not repaired in the test reaction for the compound after the incubation of step a).

9. The method of claim 8, wherein the damaged DNA comprises a base excision.

10. The method of claim 8, wherein the marker is a fluorescent dye and the quencher prevents fluorescence from the fluorescent dye.

11. The method of claim 8, wherein the marker and the quencher are each attached to opposite nucleotides of a base pair.

12. The method of claim 11, wherein the marker is attached to the nucleotide that is on the strand containing the base excision in the damaged DNA and the quencher is attached to the nucleotide that is on the intact strand of the damaged DNA.

13. The method of claim 11, wherein the test solution is a cell lysate.

14. The method of claim 13, wherein the cell lysate is from a cancerous cell.

15. A damaged DNA molecule comprising a marker attached to a first strand of the damaged DNA and a quencher attached to a second strand of the damaged DNA, wherein the quencher inhibits the release of a detectable signal from the marker when damaged DNA is in a double stranded form and the marker emits the detectable signal when at least a portion of the damaged DNA is in a single stranded form.

16. The damaged DNA molecule of claim 15, wherein the damaged DNA comprises a base excision.

17. The damaged DNA molecule of claim 16, wherein the marker is a fluorescent dye and the quencher prevents fluorescence from the fluorescent dye.

18. The damaged DNA molecule of claim 17, wherein the marker and the quencher are each attached to opposite nucleotides of a base pair.

19. The damaged DNA molecule of claim 18, wherein the marker is attached to the nucleotide that is on the strand containing the base excision in the damaged DNA and the quencher is attached to the nucleotide that is on the intact strand of the damaged DNA.

* * * * *